US006962781B1

(12) United States Patent
Williams

(10) Patent No.: US 6,962,781 B1
(45) Date of Patent: Nov. 8, 2005

(54) IN VITRO EVOLUTION OF NUCLEIC ACIDS AND ENCODED POLYPEPTIDE

(75) Inventor: Richard B. Williams, South Pasadena, CA (US)

(73) Assignee: ProteoNova, Inc., Pasadena, CA (US)

( * ) Notice: Subject to any disclaimer, the term of this patent is extended or adjusted under 35 U.S.C. 154(b) by 491 days.

(21) Appl. No.: 09/859,809

(22) Filed: May 17, 2001

Related U.S. Application Data

(60) Provisional application No. 60/206,016, filed on May 19, 2000.

(51) Int. Cl.[7] ........................ C12Q 1/68; C12N 15/00
(52) U.S. Cl. ........................ 435/6; 435/69.1; 435/69.2
(58) Field of Search ........................ 435/6, 69.1, 69.7

(56) References Cited

U.S. PATENT DOCUMENTS

| | | | | |
|---|---|---|---|---|
| 4,599,303 | A | * | 7/1986 | Yabusaki et al. ............... 435/6 |
| 5,688,670 | A | | 11/1997 | Szostak et al. |
| 5,843,701 | A | | 12/1998 | Gold et al. |
| 6,207,446 | B1 | | 3/2001 | Szostak et al. |
| 6,214,553 | B1 | | 4/2001 | Szostak et al. |
| 6,261,804 | B1 | | 7/2001 | Szostak et al. |
| 6,416,950 | B1 | | 7/2002 | Lohse et al. |
| 6,429,300 | B1 | | 8/2002 | Kurz et al. |
| 6,440,695 | B1 | * | 8/2002 | Merryman et al. ........ 435/69.1 |
| 6,602,685 | B1 | | 8/2003 | Lohse |
| 6,623,926 | B1 | | 9/2003 | Lohse et al. |
| 6,660,473 | B1 | | 12/2003 | Lohse et al. |
| 2002/0031762 | A1 | | 3/2002 | Merryman et al. |

FOREIGN PATENT DOCUMENTS

EP   WO 92/02536   2/1992

OTHER PUBLICATIONS

Sambrook et al., Molecular Cloning, a Laboratory Manual, Cold Spring Harbor Laboratory Press, pp. 8.46-8.453, and 13.3-13.18, 1989.*

An in vitro polysome display system for identifying ligands from very large peptide libraries, Larry C. Mattheakis et al., Proc. Natl. Acad. Sci. US.A., vol. 91, pp. 9022-9026, Sep. 1994.

Jean-Pierre Bachellerie et al., *Identification of the modified nucleotides produced by covalent photoaddition of hydromethyltrimethylpsoralen to RNA*, Nucleic Acids Research, Nov. 9, 1981, vol. 9, pp. 2207-2222.

William R. Kobetz and John M. Essigmann, *Solid-Phase Synthesis of Oligonucleotides Containing A Site-Specific Psoralen Derivative*, American Chemical Society, Jan. 30, 1997, vol. 119, pp. 5960-5961.

William R. Kobetz and John M. Essigmann, *An Efficient Synthesis of a Furan-Side Furocoumarin Thymidline Monoadduct*, J. Org. Chem., 1997, vol. 62, pp. 2630-2632.

T. Martin Schmeing et al., *A pre-translocational intermediate in protein synthesis observed in crystals of enzymatically active 50S subunits*. Nature Structural Biology, Mar. 2002, vol. 9, No. 3, pp. 225-230.

H. Bazin, X-X. Zhou, C. Glemarec and J. Chattopadhyaya, *Tetrahedron Letters*, vol. 28, No. 28, pp 3275-3278, 1987, "An Efficient Synthesis of Y-Nucleoside (Wyosine) by Regiospecific Methylation of $N^4$-Desmethylwyosine Using Organozinc Reagent."

* cited by examiner

*Primary Examiner*—Terry McKelvey
*Assistant Examiner*—Nancy T. Vogel
(74) *Attorney, Agent, or Firm*—Knobbe, Martens, Olson & Bear, LLP

(57) ABSTRACT

This invention relates to methods and reagents for selecting a desired protein or nucleic acid molecule by linking mRNA, with known or unknown sequences, to its translated protein to form a cognate pair. The cognate pair is selected based upon desired properties of the protein or the nucleic acid. This method also includes the evolution of a desired protein or nucleic acid molecule by amplifying the nucleic acid portion of the selected cognate pair, introducing variation into the nucleic acid, translating the nucleic acid, attaching the nucleic acid to its protein to form a second cognate pair, and re-selecting this cognate pair based upon desired properties.

31 Claims, 4 Drawing Sheets

Formation of Cognate Pair

SEQUENCE LISTING

<160> NUMBER OF SEQ ID NOS: 7

<210> SEQ ID NO 1
<211> LENGTH: 13
<212> TYPE: RNA
<213> ORGANISM: Artificial Sequence
<220> FEATURE:
<223> OTHER INFORMATION: Precursor RNA for formation of psoralentated
      RNA fragment
<220> FEATURE:
<221> NAME/KEY: modified_base
<222> LOCATION: (6)...(6)
<223> OTHER INFORMATION: n=p

<400> SEQUENCE: 1
cuagancugg agg                                                          13

<210> SEQ ID NO 2
<211> LENGTH: 13
<212> TYPE: RNA
<213> ORGANISM: Artificial Sequence
<220> FEATURE:
<223> OTHER INFORMATION: Furan sided psoralentated RNA fragment
<220> FEATURE:
<221> NAME/KEY: misc_feature
<222> LOCATION: (2)...(3)
<223> OTHER INFORMATION: psoralen bound to UA
<220> FEATURE:
<221> NAME/KEY: modified_base
<222> LOCATION: (6)...(6)
<223> OTHER INFORMATION: n=p

<400> SEQUENCE: 2
cuagancugg agg                                                          13

<210> SEQ ID NO 3
<211> LENGTH: 23
<212> TYPE: RNA
<213> ORGANISM: Artificial Sequence
<220> FEATURE:
<223> OTHER INFORMATION: Precursor RNA for psoralentated RNA fragment
<220> FEATURE:
<221> NAME/KEY: misc_feature
<222> LOCATION: (1)...(5)
<223> OTHER INFORMATION: n=g, a, u, or c
<220> FEATURE:
<221> NAME/KEY: misc_feature
<222> LOCATION: (19)...(23)
<223> OTHER INFORMATION: n=g, a, u, or c

<400> SEQUENCE: 3
nnnnnccucc agaucuagnn nnn                                               23

<210> SEQ ID NO 4
<211> LENGTH: 23
<212> TYPE: RNA
<213> ORGANISM: Artificial Sequence
<220> FEATURE:
<223> OTHER INFORMATION: Psoralentated RNA fragment
<220> FEATURE:
<221> NAME/KEY: misc_feature
<222> LOCATION: (16)...(17)
<223> OTHER INFORMATION: psoralen bound to UA
<220> FEATURE:
<221> NAME/KEY: misc_feature
<222> LOCATION: (1)...(5)
<223> OTHER INFORMATION: n=g, a, u, or c
<220> FEATURE:
<221> NAME/KEY: misc_feature
<222> LOCATION: (19)...(23)

```
<223> OTHER INFORMATION: n=g, a, u, or c

<400> SEQUENCE: 4
nnnnnccucc agaucuagnn nnn                                        23

<210> SEQ ID NO 5
<211> LENGTH: 30
<212> TYPE: DNA
<213> ORGANISM: Artificial Sequence
<220> FEATURE:
<223> OTHER INFORMATION: Fragment 3; modified tRNA; thymine at residue 8
      before pseudouridine
<220> FEATURE:
<221> NAME/KEY: modified_base
<222> LOCATION: (9)...(9)
<223> OTHER INFORMATION: n=p
<220> FEATURE:
<221> NAME/KEY: misc_feature
<222> LOCATION: (30)...(30)
<223> OTHER INFORMATION: n=puromycin

<400> SEQUENCE: 5
uccugugtnc gauccacaga auucgcaccn                                 30

<210> SEQ ID NO 6
<211> LENGTH: 43
<212> TYPE: DNA
<213> ORGANISM: Artificial Sequence
<220> FEATURE:
<223> OTHER INFORMATION: Fragment 2+3; modified tRNA; thymine at residue
      21 before pseudouridine
<220> FEATURE:
<221> NAME/KEY: modified_base
<222> LOCATION: (22)...(22)
<223> OTHER INFORMATION: n=p
<220> FEATURE:
<221> NAME/KEY: misc_feature
<222> LOCATION: (43)...(43)
<223> OTHER INFORMATION: n=puromycin
<220> FEATURE:
<221> NAME/KEY: modified_base
<222> LOCATION: (6)...(6)
<223> OTHER INFORMATION: n=p

<400> SEQUENCE: 6
cuagancugg agguccugug tncgauccac agaauucgca ccn                  43

<210> SEQ ID NO 7
<211> LENGTH: 76
<212> TYPE: DNA
<213> ORGANISM: Artificial Sequence
<220> FEATURE:
<223> OTHER INFORMATION: Fragment 1 + 2 + 3; modified tRNA; thymine at
      residue 54 before pseudouridine
<220> FEATURE:
<221> NAME/KEY: modified_base
<222> LOCATION: (39)...(39)
<223> OTHER INFORMATION: n=p
<220> FEATURE:
<221> NAME/KEY: modified_base
<222> LOCATION: (55)...(55)
<223> OTHER INFORMATION: n=p
<220> FEATURE:
<221> NAME/KEY: misc_feature
<222> LOCATION: (76)...(76)
<223> OTHER INFORMATION: n=puromycin

<400> SEQUENCE: 7
gcggauuuag cucagddggg agagcgccag acucuaganc uggagguccu gugtncgauc   60
cacagaauuc gcaccn                                                  76
```

IN VITRO EVOLUTION OF NUCLEIC ACIDS AND ENCODED POLYPEPTIDE

This application claims the benefit from provisional application U.S. Ser. No. 60/206,016 to Williams, filed May 19, 2000, the entirety of which is incorporated by reference herein.

BACKGROUND OF THE INVENTION

1. Field of the Invention

The present invention relates to compositions and methods for the selection of nucleic acids and polypeptides.

2. Description of the Related Art

Ligand-receptor interactions are of interest for many reasons, from elucidating basic biological site recognition mechanisms to drug screening and rational drug design. It has been possible for many years to drive in vitro evolution of nucleic acids by selecting molecules out of large populations that preferentially bind to a selected target, then amplifying and mutating them for subsequent re-selection (Tuerk and Gold, Science 249:505 (1990), herein incorporated by reference).

The ability to perform the selection process with proteins would be extremely useful. This would permit in vitro design and production of proteins that bind specifically to chosen ligands. The use of proteins, as compared to nucleic acids, is particularly advantageous because the twenty diverse amino acid side chains in proteins have far more binding possibilities than the four similar chains in nucleic acid side. Further, many biologically and medically relevant ligands bind proteins.

Both nucleic acid and protein evolution methods require access to a large and highly varied population of test molecules, a way to select members of the population that exhibit the desired properties, and the ability to reproduce the selected molecules with mutated variations to obtain another large population for subsequent selection.

Prior attempts to develop a protein evolution method were primarily limited by the inability of the proteins to reproduce themselves and the inability to link a polypeptide's encoding mRNA with the translated product. Additionally, the generation of large peptide libraries and screening methods have, until recently, required that the process have an in vivo expression step. Examples include yeast two- or three-hybrid, yeast display and phage display methods (Fields and Song, Nature 340:245 (1989); Licitra and Liu, PNAS 93:12817 (1996); Boder and Wittrup, Nat Biotechnol 15:553 (1997); and Scott and Smith, Science 249:386 (1990)). In vivo methods suffer from various disadvantages, including a limited library size and cumbersome screening steps. Additionally, undesired selective pressures can be placed on the generation of variants by cellular constraints of the host.

In vitro methods have been developed more recently, using prokaryotic and eukaryotic in vitro translation systems, such as ribosome display. (Mattheakis et al., PNAS 91:9022 (1994); Hanes and Plückthun, PNAS 94:4937 (1997); Jermutus et al., Current Opinion in Biotechnology 9:534 (1998), all herein incorporated by reference). These methods link the protein and its encoding mRNA with the ribosome and the entire complex is screened against a ligand of choice. Potential disadvantages of this method include the large size of the ribosome, which could interfere with the screening of the attached, and relatively tiny, protein.

In 1997, two groups of workers developed an in vitro method of attaching a protein to its coding sequence during translation by using the ribosomal peptidyl transferase with puromycin attached to a linker DNA (Szostak et al., International Patent Publication WO 98/31700; Roberts and Szostak PNAS 94:12297 (1997); Nemoto et al., FEBS Letters 414:405 (1997), all herein incorporated by reference). Once the coding sequence and peptides are linked, the peptides are exposed to a selected ligand. Selection or binding of the peptide by the ligand also selects the attached coding sequence, which can then be reproduced by standard means. Both Roberts and Szostak and Nemoto et al. used the technique of attaching a puromycin molecule to the 3' end of a coding sequence by a DNA linker or other non-translatable chain. Puromycin is a tRNA acceptor stem analog which accepts the nascent peptide chain under the action of the ribosomal peptidyl transferase and binds it stably and irreversibly, thereby halting translation. These methods suffer from certain disadvantages. For example, the coding sequence encoding each peptide must be known and be modified both initially and between each selection. Thus, the methods of Roberts and Nemoto cannot be used to select native unknown mRNAs. Further, the modification of the coding sequence adds several steps to the process. Finally, the attached puromycin on the linker molecules may compete in the translation reaction with the native tRNAs for the A site on the ribosome reading its coding sequence or a nearby ribosome, and could thus "poison" the translation process, just as would unattached puromycin in the translation reaction solution. Inadvertent interactions between puromycin and ribosomes could result in two kinds of reaction non-specificity: prematurely shortened proteins and proteins attached to the wrong message. There are reports in the prior art that indicate that the avidity of the A site and the peptidyl transferase for the puromycin may be modulated by $Mg^{++}$ concentration (Roberts, Curr. Opin. Chem. Biol. 3:268 (1999), herein incorporated by reference). Although $Mg^{++}$ concentration may be titrated to control for the first kind of non-specificity, i.e. premature termination of translation, it will not affect the second type, i.e. inaccurate mRNA-protein linkage.

Thus, a need exists for an in vitro nucleic acid-based protein evolution system which does not necessarily require initial knowledge of the nucleic acid's sequence or repeated chemical modification of the nucleic acids, and which can accurately link a mRNA to its protein.

SUMMARY OF THE INVENTION

The present invention provides compositions and methods to select and evolve desired properties of proteins and nucleic acids. In various embodiments, the current invention provides modified tRNA's and tRNA analogs. Other embodiments include methods for generating polypeptides, assays enabling selection of individual members of the population of polypeptides having desired characteristics, methods for amplifying the nucleic acids encoding such selected polypeptides, and methods for generating new variants to screen for enhanced properties.

In several embodiments, the present invention permits the attachment of a protein to its message without requiring modification of native mRNA, although modified mRNA may still be used. The specificity of the methods embodied in various aspects of the current invention are determined by the specificity of the codon-anticodon interaction.

In a preferred embodiment, the invention permits the selection of nucleic acids by selecting the proteins for which they code. This may be accomplished by connecting the protein to its cognate mRNA at the end of translation, which in turn is done by connecting both the protein and mRNA to a tRNA or tRNA analog.

A preferred embodiment of the invention includes a tRNA molecule capable of covalently linking a nucleic acid encoding a polypeptide and the polypeptide to the tRNA, wherein the linkage of the nucleic acid occurs on a portion of the tRNA other than the linkage of the polypeptide, the tRNA comprising a linking molecule associated with the anticodon of the tRNA. Preferably, an amino acid or amino acid analog is attached to the 3' end of a tRNA molecule by a stable bond to generate a stable aminoacyl tRNA analog (SATA).

Other embodiments include a mRNA comprising a psoralen, preferably located in the 3' region of the reading frame, more preferably at the most 3' codon of the reading frame, most preferably at the 3' stop codon of the reading frame. In preferred embodiments, linkage between the tRNA and the mRNA is a cross-linked psoralen molecule, more preferably a furan-sided psoralen monoadduct.

Several embodiments of the present invention include a method of stably linking a nucleic acid, a tRNA, and a polypeptide encoded by the mRNA together to form a linked mRNA-polypeptide complex. In a preferred embodiment, the nucleic acid is an mRNA. The method can further comprise providing a plurality of distinct nucleic acid-polypeptide complexes, on, for example, an array, providing a ligand with a desired binding characteristic, contacting the complexes with the ligand, removing unbound complexes, and recovering complexes bound to the ligand.

Several methods of the current invention involve the evolution of nucleic acid molecules and/or proteins. In one embodiment, this invention comprises amplifying the nucleic acid component of the recovered complexes and introducing variation to the sequence of the nucleic acids. In other embodiments, the method further comprises translating polypeptides from the amplified and varied nucleic acids, linking them together using tRNA, and contacting them with the ligand to select another new population of bound complexes. Several embodiments of the present invention use selected protein-mRNA complexes in a process of in vitro evolution, especially the iterative process in which the selected mRNA is reproduced with variation, translated and again connected to cognate protein for selection.

DETAILED DESCRIPTION OF THE PREFERRED EMBODIMENT

Figure 3:
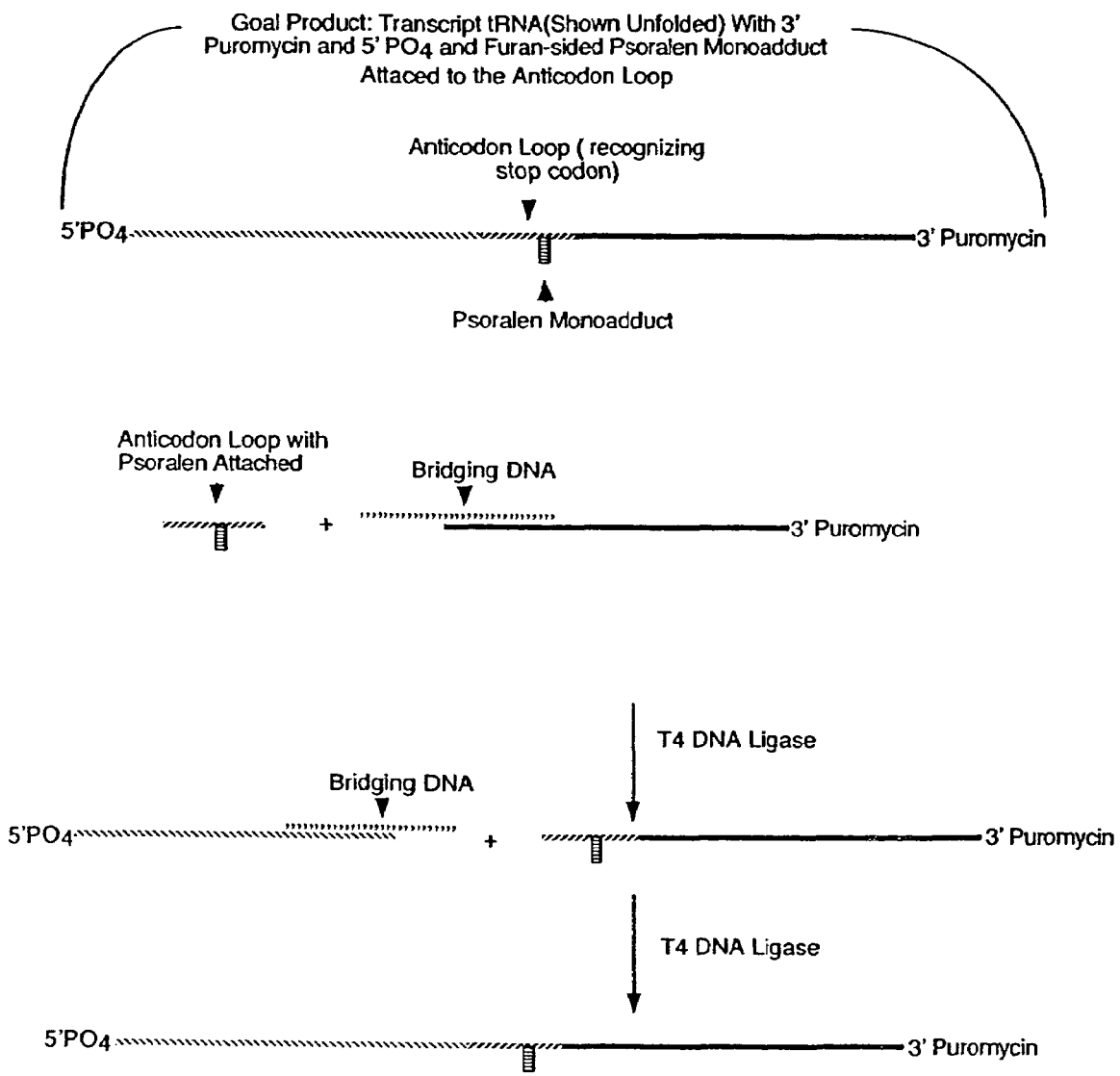
FIG. 3 illustrates one method of construction of a tRNA molecule of the invention. In this embodiment, the 5' end of a tRNA, a nucleic acid encoding an anticodon loop and having a molecule capable of stably linking to mRNA (here, psoralen), and the 3' end of tRNA modified with a terminal puromycin molecule are ligated to form a complete modified tRNA for use in the in vitro evolution methods of the invention.

Various aspects of the present invention use a tRNA mechanism that links messenger RNA (mRNA) to its translated protein product, forming a "cognate pair." In several embodiments, mRNAs whose sequence is not known can be expressed, its protein characterized through a selection process against a ligand with desired or selected properties, and nucleic acid evolution—resulting in protein evolution—can be performed in vitro to arrive at molecules with enhanced properties. The cognate pairs are preferably attached via a linking tRNA, modified tRNA, or tRNA analog. In a preferred embodiment, the tRNA is connected to the nascent peptide by the ribosomal peptidyl transferase and to the mRNA through an ultraviolet induced cross link between the anticodon of the tRNA or tRNA analog and the codon of the RNA message. This can be done by, for example thiouracil, but in a preferred method, the linker is a psoralen crosslink made from a psoralen monoadduct pre-placed on either the mRNA or preferably on the tRNA anticodon of choice. Preferably, a tRNA stop anticodon is selected. A stop codon/anticodon pair selects for full length transcripts. One skilled in the art will understand that a mRNA not having a stop codon may also be used and that any codon or nucleic acid triplet may be used. A tRNA having an anticodon which is not naturally occurring can be synthesized according to methods known in the art (e.g. FIG. 3).

The terms "protein," "peptide," and "polypeptide" are defined herein to mean a polymeric molecule of two or more units comprised of amino acids in any form (e.g., D- or L-amino acids, synthetic or modified amino acids capable of polymerizing via peptide bonds, etc.), and these terms may be used interchangeably herein.

The term "pseudo stop codon" is defined herein to mean a codon which, while not naturally a nonsense codon, prevents a message from being further translated. A pseudo stop codon may be created by using a "stable aminoacyl tRNA analog" or SATA, as described below. In this manner, a pseudo stop codon is a codon which is recognized by and binds to a SATA. Another method by which to create a pseudo stop codon is to create an artificial system in which the necessary tRNA having an anticodon complementary to the pseudocodon is substantially depleted. Accordingly, translation will stop when the absent tRNA is required, i.e.

at the pseudo stop codon. One skilled in the art will appreciate that are numerous ways to create a pseudo stop codon as defined herein.

The formation of connections between mRNA and its protein product generally requires a tRNA or tRNA analog with certain characteristics. In several embodiments of the current invention, the tRNA or tRNA analog will have a stable peptide acceptor. This modification changes the tRNA or tRNA analog such that after it accepts the nascent peptide chain by the action of the ribosomal peptidyl transferase, it holds the chain in a stable manner such that the peptidyl transferase cannot detach it. This may be accomplished by using a bond such as a 2' ester on a 3' deoxy adenosine or an amino "acyl $tRNA_{ox-red}$" which can bind to the ribosome, accept the peptide chain, and then not act as a donor in the next transpeptidation (Chinali et al., Biochem. 13:3001 (1974); Krayevsky and Kukhanova, Prog. Nuc. Acid Res 23:1 (1979) and Sprinzl and Cramer Prog. Nuc. Acid Res 22:1 (1979), all herein incorporated by reference).

In a preferred embodiment, an amino acid or amino acid analog is attached to the 3' end of the tRNA or tRNA analog by a stable bond. This stable bond contrasts the labile, high energy ester bond that connects these two in the native structure. The stable bond not only protects the bond from the action of the peptidyl transferase, but also preserves the structure during subsequent steps. For convenience, this modified tRNA or tRNA analog will be referred to as a "stable aminoacyl tRNA analog" or SATA. As used herein, a SATA is an entity which can recognize a selected codon such that it can accept a peptide chain by the action of the ribosomal peptidyl transferase when the cognate codon is in the reading position of the ribosome. The peptide chain will be bound in such a way that the peptide is bound stably and cannot be unattached by the peptidyl transferase. Preferably, the selected codon is recognized by hydrogen bonding.

One method for creating a SATA was published in 1973 (Fraser and Rich, PNAS 70:2671 (1973), herein incorporated by reference). This method involves the conversion of a tRNA, or tRNA analog, to a 3'-amino-3'-deoxy tRNA. This is accomplished by adding a 3'-amino-3'-deoxy adenosine to the end of a native tRNA with tRNA nucleotidyl transferase after removing the native adenosine from it with snake venom phosphodiesterase. This modified tRNA is then charged with an amino acid by the respective aminoacyl tRNA synthetase (aaRS). Fraser and Rich used an aaRS in which the tRNA is charged on the 3', rather than the 2', hydroxyl. The amino acid is bound to the tRNA by a stable amide bond rather than the usual labile high-energy ester bond. Thus, when it accepts a peptide from ribosomal peptidyl transferase it will stably hold the peptide and not be able to donate it to another acceptor.

In a preferred method, the SATA will be attached to the translated message by a psoralen cross link between the codon and anticodon. Psoralen cross links are preferentially made between sequences that contain complementary 5' pyrimidine-purine 3' sequences especially UA or TA sequences (Cimino et al., Ann. Rev. Biochem. 54:1151 (1985), herein incorporated by reference). The codon coding for the SATA, or the linking codon, can be PYR-PUR-X or X-PYR-PUR, so that several codons may be used for the linking codon. Conveniently, the stop or nonsense codons have this configuration. Using a codon that codes for an amino acid may require minor adjustments to the genetic code, which could complicate some applications. Therefore, in a preferred embodiment, a stop codon is used as the linking codon and the SATA functions as a nonsense suppressor in that it recognizes the linking codon. One skilled in the art, however, will appreciate that, with appropriate adjustments to the system, any codon can be used.

Fraser and Rich did their work in *E. coli*, but the most effective in vitro translation systems are in eukaryotes The use of prokaryotic suppressors in eukaryotic translation systems appears to be feasible (Geller and Rich Nature 283:41 (1980); Edwards et al PNAS 88:1153 (1991); Hou and Schimmel Biochem 28:6800 (1989), all herein incorporated by reference). They are primarily limited by the resident aaRS's. This limitation is overcome by various embodiments of the present invention because the tRNA or analog can be charged in the prokaryotic system and then purified according to established methods (Lucas-Lenard and Haenni, PNAS 63:93 (1969), herein incorporated by reference).

In several embodiments of the current invention, acceptor stem modifications suitable for use in the tRNAs and analogs can be produced by various methods known in the art. Such methods are found in, for example, Sprinzl and Cramer, Prog. Nuc. Acid Res. 22:1 (1979), herein incorporated by reference. In an alternative embodiment, "transcriptional tRNA", i.e. the sequence of the tRNA as it would be transcribed rather than after the post-transcriptional processing, leads to the atypical and modified bases that are common in tRNAs. These transcriptional tRNAs are capable of functioning as tRNAs (Dabrowski et al., EMBO J. 14:4872, 1995; and Harrington et al., Biochem. 32: 7617, 1993, both herein incorporated by reference). Transcriptional tRNA can be produced by transcription or can be made by connecting commercial RNA sequences (such as those available from Dharmacon Research Inc., Boulder, Colo.) together, piece-wise as in FIG. 3, or in some combination of established methods. For instance, the 5' phosphate and 3' puromycin are commercially available attached to oligoribonucleotides. These pieces can be connected together using T4 DNA ligase, as is well-known in the art (Moore and Sharp, Science 256:992, 1992, herein incorporated by reference). Alternatively, in a preferred embodiment, T4 RNA ligase is used (Romaniuk and Uhlenbeck, Methods in Enzymology 100:52 (1983), herein incorporated by reference).

Figure 4:
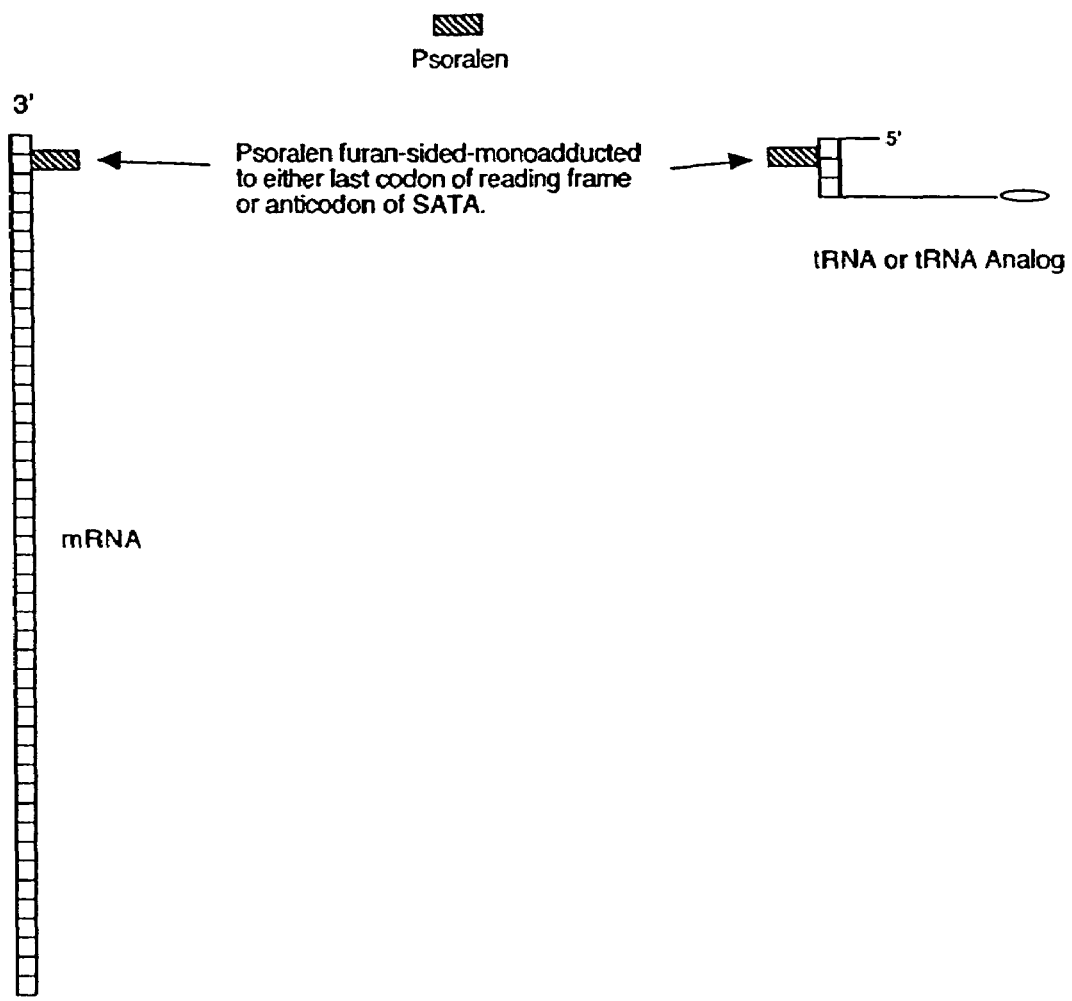
FIG. 4 describes two alternative embodiments by which the crosslinking molecule psoralen can be positioned to be capable of linking the mRNA with the tRNA in the methods of the invention. A first embodiment includes linking the psoralen monoadduct to the mRNA, and a second embodiment includes linking the psoralen to the anticodon of the tRNA. Psoralen can either be monoadducted to the anticodon or the 3' terminal codon of the reading frame for known or partially known messages. This can be done in a separate procedure from translation, i.e. before translation occurs.

In several embodiments of the present invention, psoralen is monoadducted to the SATA by construction of a tRNA from pieces including a psoralen linked oligonucleotide (FIG. 3) or by monoadduction to a native or modified tRNA or analog (FIG. 4).

In several embodiments, translation will stop when the nascent protein is attached to the SATA by the peptidyl transferase. When a large number of ribosomes are in this position the SATA and the mRNA will be connected with UV light. In a preferred method this will be accomplished by having a psoralen crosslink formed. Psoralens have a furan side and a pyrone side, and they readily intercalate between complementary base pairs in double stranded DNA, RNA, and DNA-RNA hybrids (Cimino et al., Ann. Rev. Biochem. 54:1151 (1985), herein incorporated by reference). Upon irradiation with UV, preferably in the range of 320 nm to 400 nm, cross linking will take place and leave the staggered pyrimidines covalently bound. By either forming crosslinks and photo reversing them or by using selected wavelengths, it is possible to form monoadducts, described more fully below. These will be either pyrone sided or furan sided monoadducts. Upon further irradiation, the furan sided monoadducts can be covalently crosslinked to complementary base pairs. The pyrone sided monoadducts cannot be further crosslinked. The formation of the furan sided psoralen monoadduct (MAf) is also done according to established methods. In a preferred method, the psoralen is attached to the anticodon of the SATA. However, psoralen can also be attached at the end of the reading frame of the message, as depicted in FIG. 4.

Methods for large scale production of purified MAf on oligonucleotides are described in the literature (e.g., Speilmann et al., PNAS 89:4514, 1992, herein incorporated by reference), as are methods that require less resources, but have some non-cross-linkable pyrone sided psoralen monoadduct contamination (e.g., U.S. Pat. No. 4,599,303; Gamper et al., J. Mol.Biol. 197:349 (1987); Gamper et al., Photochem. Photobiol. 40:29 (1984), both herein incorporated by reference). In several embodiments of the current invention, psoralen labeling is accomplished by using either method. In a preferred embodiment, furan sided monoadducts will be created using visible light, preferably in the range of approximately 400 nm–420 nm, according to the methods described in U.S. Pat. No. 5,462,733 and Gasparro et al., Photochem. Photobiol. 57:1007 (1993), both herein incorporated by reference. In one aspect of this invention, a SATA with a furan sided monoadduct or monoadducted oligonucleotides for placement on the 3' end of mRNAs, along with a nonadducted SATA are provided as the basis of a kit.

Use of the SATA and the monoadduct in several embodiments of the current invention is particularly advantageous for in vitro translation systems. However, one skilled in the art will appreciate that in situ systems can also be used. Various embodiments of the current invention will be applicable to any in vitro translation system, including, but not limited to, rabbit reticulocyte lysate (RLL), wheat germ, $E.$ $coli$, yeast lysate systems, etc. Many embodiments of the current invention are also well-suited for use in hybrid systems where components of different systems are combined.

tRNAs aminoacylated on a 3' amide bond are reported not to combine with the elongation factor EF-TU which assists in binding to the A site (Sprinzl and Cramer, Prog. Nuc. Acid Res. 22:1 (1979), herein incorporated by reference). Such modified tRNAs do, however, bind to the A site. This binding of 3' modified tRNAs can be increased by changing the $Mg^{++}$ concentration (Chinali et al., Biochem. 13:3001 (1974), herein incorporated by reference). The appropriate concentrations of and/or molar ratios of SATA and Mg++can be determined empirically. If the concentration or A site avidity of SATA is too high, the SATA could compete with native tRNAs for non-cognate codons i.e., could function much like puromycin and stall translation. If the concentration or A site avidity of SATA is too low, the SATA might not effectively compete with the release factors, i.e., it would not act as an effective nonsense suppressor tRNA. The balance between these can be determined empirically.

It is also believed that the elongation factor aids in proofreading the codon-anticodon recognition. The error rate in the absence of elongation factor and the associated GTP hydrolysis is estimated to be 1 in 100 for codons one nucleotide away (Voet and Voet, Biochemistry $2^{nd}$ ed. pp. 1000–1002 (1995), John Wiley and Sons, herein incorporated by reference). In a preferred embodiment, UAA is used as the linking codon. For UAA as the linking codon, there are 7 non stop codons which differ by one amino acid. This is 7/61 or about 11.5% of the non stop codons. One can estimate the probability of miscoding a given codon as $(0.01)(0.115)=1.15 \times 10^{-3}$ miscodes per codon. Thus, one would expect a miscode about every 870 codons, a frequency which will not substantially impair performance of various methods of the current invention. In an alternative embodiment, UAG is used as the linking codon.

In several embodiments, appropriate concentrations of SATA and $Mg^{++}$ are used in the in vitro translation system, e.g. RRL, in the presence of the mRNA molecules in the pool, causing translation to cease when the ribosome reaches the codon which permits the SATA to accept the peptide chain (the linking codon described above). Within a short time, most of the linking codons will be occupied by SATAs within ribosomes. In a preferred embodiment, the system then will be irradiated with UV light, preferably at approximately 320 nm to 400 nm. Nucleic acids are typically transparent to, i.e. do not absorb, this wavelength range. Upon irradiation, the psoralen monoadduct will convert to a crosslink connecting the anticodon and the codon by a stable covalent bond.

In a preferred embodiment, the target mRNA is preselected. In another embodiment, the target mRNA is artificially produced. In an alternative embodiment, the target consists of messages native to the system under investigation, which may be unknown and/or unidentified. The ability to use unknown and/or unidentified mRNAs is a particular advantage of several embodiments of the current invention.

In several embodiments, once all the nascent proteins are connected to their cognate mRNAs, the ribosomes are released or denatured. Preferably, this is accomplished by the depletion of $Mg^{++}$ through dialysis, simple dilution, or chelation. One skilled in the art will understand that other methods, including, but not limited to, denaturation by changing the ionic strength, the pH, or the solvent system can also be used.

In several embodiments of the invention, the selection of cognate pairs will be based upon affinity binding of proteins according to any of a variety of established methods, including, but not limited to, arrays, affinity columns, immunoprecipitation, and many high throughput screening procedures. A variety of ligands may also be used, including, but not limited to, proteins, nucleic acids, chemical compounds, polymers and metals. In addition, cell membranes or receptors, or even entire cells may be used to bind the cognate pairs. The selection can be positive or negative. That is, the selected cognate pairs can be those that do bind well to a ligand or those that do not. For instance, for a protein to accelerate a thermodynamically favorable reaction, i.e., act as an enzyme for that reaction, it should bind both the substrate and a transition state analog. How ever, the transition state analog should be bound much more tightly than the substrate. This is described by the equation $$\frac{k_{enzyme}}{k_{\varphi enzym}} = \frac{K_{trans}}{K_{subst}}$$

where the ratio of the rate of the reaction with the enzyme, $k_{enzyme}$ to the rate without, $k_{enzyme}$, is equal to the ratio of the binding of the transition state to the enzyme $K_{trans}$ over the binding of the substrate to the enzyme $K_{subst}$ (Voet and Voet, Biochemistry $2^{nd}$ ed. p. 380, (1995), John Wiley.

In a preferred embodiment, proteins which compete poorly for binding to the substrate but compete well for binding to the transition state analog are selected. Operationally, this may be accomplished by taking the proteins that are easily eluted from a matrix with substrate or substrate analog bound to it and are the most difficult to remove from matrix with transition state analog bound to it.

By sequentially repeating this selection and reproducing the proteins through replication and translation of the nucleic acid of the cognate pairs, an improved enzyme should evolve. Affinity to one entity and lack of affinity to another in the same selection process is used in several embodiments of the current invention. Selection can also be done by RNA in many embodiments.

Once the selection has identified a population of cognate pairs it may be convenient to detach the mRNA strand from the SATA to reproduce it. This is not always necessary but can be accomplished by irradiating the pairs with UV, preferably at approximately 313 nm or just below. This has been identified as a wave length that will photoreverse the psoralen crosslink to MAf and damage the nucleic acid minimally. The ratio of photoreversal to nucleic acid damage is estimated to be 1 photoreversal for damage to 1 in 600 bases (Cimino et al., Biochem 25:3013 (1986), herein incorporated by reference).

One skilled in the art will appreciate that the mRNAs can be reproduced in many ways, including, but not limited to, by RNA-dependent RNA polymerases or by reverse transcription and PCR. This can take place using mRNAs separated from the cognate pairs, e.g., using poly T or poly U to hybridize to the poly A tails of, for instance, native unknown messages or by leaving the cognate pairs intact and using oligonucleotide primers that hybridize partially into the reading frame for known messages. Alternatively, commercial kits for rapid amplification of cDNA ends may be used. When this is used to evolve proteins and not just to select them, it would be preferable to sample at least one amino acid substitution at each position in the protein.

The Replication Threshold

A nominal minimum number of replications for efficient evolution may be estimated using the following formulae. If there is a sequence which is n sequences in length, with a selective improvement r mutations away with a mutation rate of p, the probability of generating the selective improvement on replication may be determined as follows:

For r=1, probability of a mutation at the right point, p, times the probability that it mutated to the right one of the three nucleotides that are different from the starting point, ⅓, times the probability that the other n-1 sites remain unmutated, (1-p)(n-r), or $$P_r = \left(\frac{p}{3}\right)^1 (1-p)^{(n-1)}$$

where, P=the probability of attaining a given change r mutations away. More generally, for all r values:

$$P_r = \left(\frac{p}{3}\right)^r (1-p)^{(n-r)}$$

It is instructive to compare the chances of finding an advantage one mutation away with the chances three mutations away. This is because, given the triplet genetic code, any given codon can only change into nine other codons in one mutation. Indeed, it turns out that no codon can actually change into nine other amino acid codes in one mutation. The maximum number of amino acids that can be accessed in one mutation is seven amino acids and there are only eight codons of the sixty-four that can do this. Most codons have five or six out of nineteen other amino acids within one mutation. To reach all nineteen amino acids that are different from the starting one requires, in general, three mutations. These three mutations cannot be sequential since the two intervening ones will not, in general, be selectively advantageous. Therefore we need to use steps that are, at least, three mutations in size (r=3) to use all 20 amino acids.

For a mutation rate of 0.0067, which is that reported for "error-prone PCR", using a message of 300 nucleotides, which gives a short protein of 100 amino acids:

$$P_3 = 1.51 \times 10^{-9}$$

Therefore, one would expect to need a threshold of:

$$\frac{1}{1.51 \times 10^{-9}} = 6.64 \times 10^8$$

replications at that mutation rate to reasonably expect to reach the next amino acid that is advantageous. This is not the replication to use since the binomial expansion shows that over ⅓ of trials (actually about 1/e) would not contain the given sequence with selective advantage.

A poisson approximation for large n and small p for a given $\mu$ can be calculated so that we can compute the general term when n is, say, of the order $10^9$ and p is of the order $10^{-9}$. The general term of the approximation is:

An amplification factor of greater than approximately 6/P ensures that evolution will progress with the use of all amino acids. This is useful when the production of novel proteins precludes the use of "shuffling" of preexisting proteins.

Limits on Purification

Given a reversible binding where B and C compete for A:

AB ↔ A+B  AC ↔ A+C $$k_B = \frac{[A][B]}{[AB]} \quad (1)$$

$$k_C = \frac{[A][C]}{[AC]}$$

$$[B] = k_B \frac{[AB]}{[A]}$$

$$[C] = k_C \frac{[AC]}{[A]} \quad (2)$$

The total concentrations can be expressed:

$$[B]_T = [B] + [AB] \quad (3)$$

$$[C]_T = [C] + [AC] \quad (4)$$

Dividing (3) by (4)

$$\frac{[B]_T = [B] + [AB]}{[C]_T = [C] + [AC]}$$

And substituting (1) and (2) for [B] and [C]:

$$\frac{[B]_T = k_B\left[\frac{AB}{A}\right] + [AB]}{[C]_T = k_C\left[\frac{AC}{A}\right] + [AC]}$$

Rearranging:

$$\frac{[B]_T}{[C]_T} = \frac{[AB]\left(\frac{k_B + [A]}{[A]}\right)}{[AC]\left(\frac{k_C + [A]}{[A]}\right)}$$

Canceling the [A]'s in the numerator and denominator:

$$\frac{[B]_T}{[C]_T} = \frac{[AB](k_B + [A])}{[AC](k_C + [A])}$$

Finally rearranging:

$$\frac{[AB]}{[AC]} = \frac{[B]_T(k_C + [A])}{[C]_T(k_B + [A])}$$

$$\frac{(k_C + [A])}{(k_B + [A])}$$

(Enrichment Factor)

The above factor is termed the "Enrichment Factor". The ratio of the total components is multiplied by this factor to calculate the ratio of the bound components, or the enrichment of B over C. The maximum enrichment factor is $k_C/k_B$, when the [A] is significantly smaller than $k_C$ or $k_B$.

The enrichment is limited by the ratio of binding constants. To enrich a scarce protein that is bound 100 times as strongly as its competitors, the ratio of that protein to its competitors is increased by 1 million with 3 enrichments. To enrich a protein that only binds twice as strongly than its competitors, 10 enrichment cycles would gain only an enrichment of ~1000.

The following Example illustrate various embodiments of the present invention and are not intended in any way to limit the invention.

EXAMPLE 1

Production of the SATA

Figure 1:
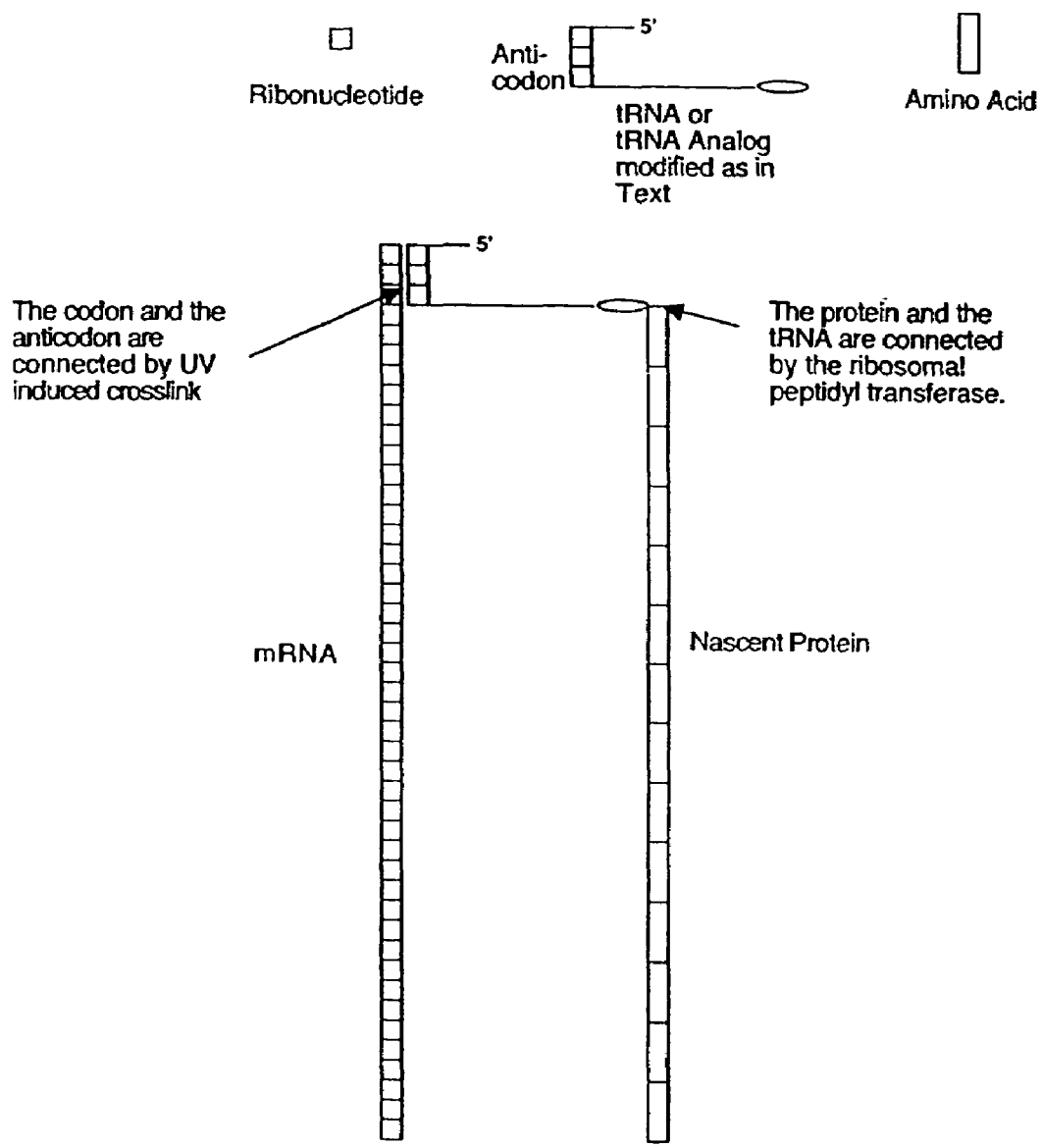
FIG. 1 illustrates schematically one example of the complex formed by the mRNA and its protein product when linked by a modified tRNA or analog. As shown, a codon of the mRNA pairs with the anticodon of a modified tRNA and is covalently crosslinked to a psoralen monoadduct by UV irradiation. The translated polypeptide is linked to the modified tRNA via the ribosomal peptidyl transferase. Both linkages occur while the mRNA and nascent protein are held in place by the ribosome.
Figure 2:
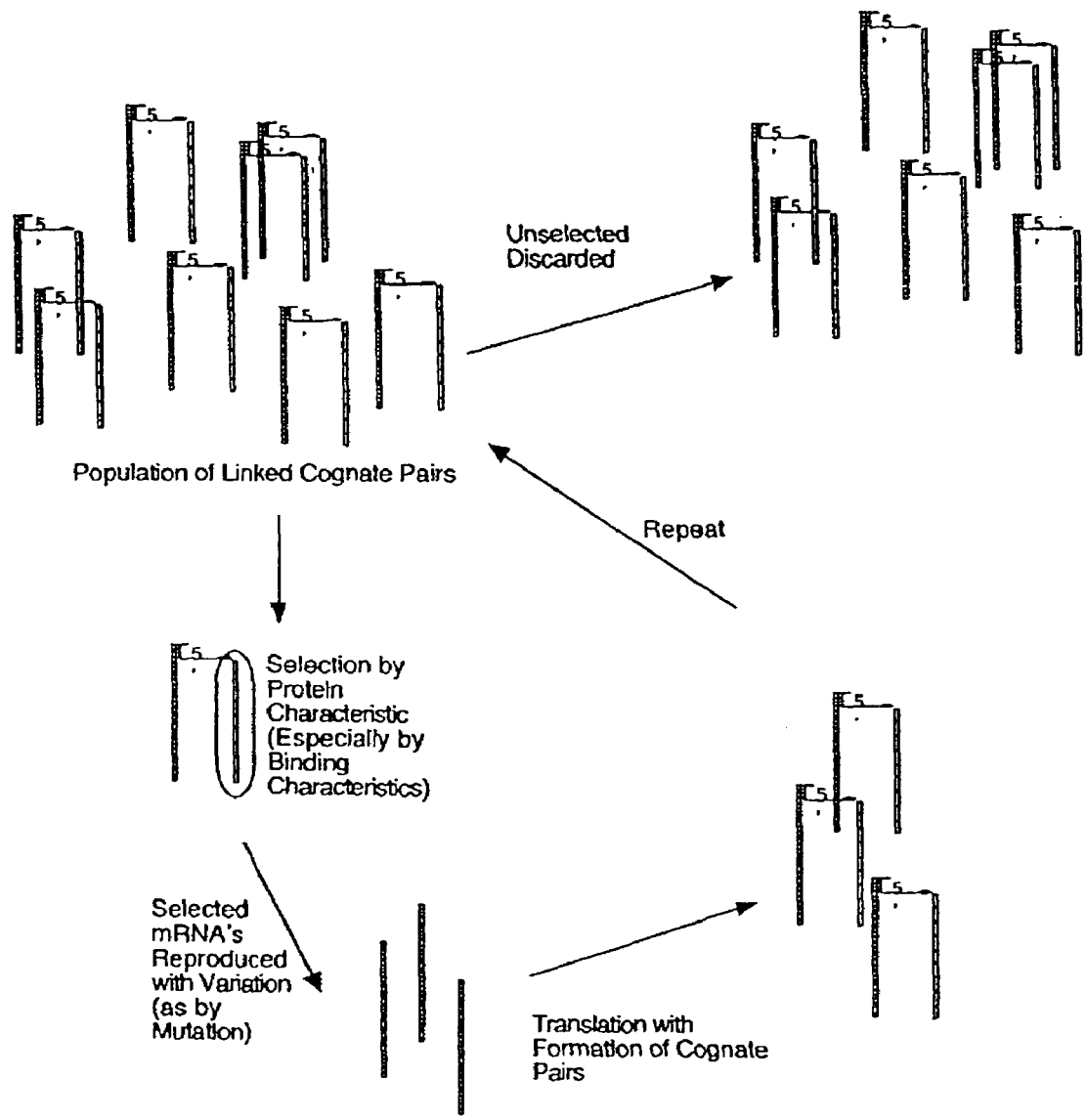
FIG. 2 illustrates schematically an example of the in vitro selection and evolution process, wherein the starting nucleic acids and their protein products are linked (e.g., according to FIG. 1) and are selected by a particular characteristic exhibited by the protein. Proteins not exhibiting the particular characteristic are discarded and those having the characteristic are amplified with variation, preferably via amplification with variation of the mRNA, to form a new population. In various embodiments, nonbinding proteins will be selected. The new population is translated and linked via a modified tRNA or analog, and the selection process is repeated. As many selection and amplification/mutation rounds as desired can be performed to optimize the protein product.

One skilled in the art will understand that the SATA can be produced in a number of different ways. For example, in a preferred embodiment, three fragments (FIG. 1) are purchased from a commercial source (i.e. Dharmacon Research Inc., Boulder, Colo.). Modified bases and a fragment 3 with a pre-attached puromycin on its 3' end and a $PO_4$ on its 3' end are included, all of which are available commercially. Three fragments are used to facilitate manipulation of the fragment 2 in forming the monoadduct.

Yeast tRNAA1a or yeast tRNAPhe is used; however, sequences can be chosen widely from known tRNA's. Preferably, sequences with only a limited number of U's in the portion that corresponds to the fragment 2 are used. Using a sequence with only a few U's is not necessary because psoralen preferentially binds 5'UA3' sequences (Thompson J. F, et al Biochemistry 21:1363, herein incorporated by reference). However, there would be less doubly adducted product to purify out if such a sequence was used.

The fragment 2 is used in a helical conformation to induce the psoralen to intercalate. Accordingly, a complementary strand is required. RNA or DNA is used, and a sequence, such as poly C to one or both ends, is added to facilitate separation and removal after monoadduct formation is accomplished.

The fragment 2 and the cRNA are combined in buffered 50 mM NaCl solution. The Tm is measured by hyperchromicity changes. The two molecules are re-annealed and incubated for 1 hour with the selected psoralen at a temperature ~10° C. less than the Tm. The psoralen is selected based upon the sequence used. For instance, a relatively insoluble psoralen, such as 8 MOP, has a higher sequence stringency but may need to be replenished. A more soluble psoralen, such as AMT, has less stringency but will fill most sites. Preferably, HMT is used. If a fragment 2 is chosen that contains more non-target U's, a greater stringency is desired. Decreasing the temperature or increasing ionic strength by adding $Mg^{++}$ is also used to increase the stringency.

Following incubation, psoralen is irradiated at a wavelength greater than approximately 400 nm. The irradiation depends on the wavelength chosen and the psoralen used. For instance, approximately 419 nm 20–150 J/cm2 is preferably used for HMT. This process will result in an almost entirely furan sided monoadduct.

Purification of Monoadduct

The monoadduct is then purified by HPLC as described in Sastry et al, J. Photochem. Photobiol. B Biol. 14:65–79, herein incorporated by reference. The fact that fragment 2 is separate from fragment 3 facilitates the purification step because, generally, purification of monoadducts 25 mer is difficult (Spielmann et al. PNAS 89: 4514–4518, herein incorporated by reference).

Ligation of Fragment 2 and 3

The fragment 2 is ligated to the fragment 3 using T4 RNA ligase. The puromycin on the 3' end acts as a protecting group this is done as per Romaniuk and Uhlenbeck, Methods in Enzymology 100:52–59 (1983), herein incorporated by reference. Joining of fragment 2+3 to the 3' end of fragment 1 is done according to the methods described in Uhlenbeck, Biochemistry 24:2705–2712 (1985), herein incorporated by reference. Fragment 2+3 is 5' phosphorylated by polynucleotide kinase and the two half molecules are annealed.

In an alternative method, significant quantities of furan sided monoadducted U will be formed by hybridizing poly UA to itself and irradiating as above. The poly UA will then be enzymatically digested to yield furan sided U which will be protected and incorporated into a tRNA analog by nucleoside phosphoramidite methods. Other methods of forming the psoralen monoadducts include the methods described in Gamper et al., J. Mol. Biol. 197: 349 (1987); Gamper et al., Photochem. Photobiol. 40:29, 1984; Sastry et al, J. Photochem. Photobiol. B Biol. 14:65–79; Spielmann et al. PNAS 89:4514–4518, U.S. Pat. No. 4,599,303, all herein incorporated by reference.

SATAs generated by the methods described above will read UAG (anticodon CUA). Additionally, UAA or UGA will be also be used. In various embodiments, any message that has the stop codon that is selected as the "linking codon" is used.

EXAMPLE 2

Production of Psoralenated Furan Sided Monoadducts from CUAGA CUGGAGG RNA Fragments UVLight Exposure Of RNA:DNA Hybrids Equal volumes of 3 ng/ml RNA:cRNA hybrid segments and of 10 μg/ml HMT both comprised of 50 mM NaCl are transferred into a new 1.5 ml capped polypropylene microcentrifuge tube and incubated at 37° C. for 30 minutes in the dark. This was then transferred onto a new clean culture dish. This is positioned in a photochemical reactor (419 nm peak Southern New England Ultaviolet Co.) at a distance of about 12.5 cm so that irradiance is ~6.5 mW/cm2 and irradiated for 60–120 minutes.

Removal of Low Molecular Weight Protoproducts

100 μl of chloroform-isoamyl alcohol (24:1) is pipetted and mixed by vortex. Mixture is centrifuged for 5 minutes at 15000×g in a microcentrifuge tube. The chloroform-isoamyl alcohol layer is removed with a micropipet. The chloroform-isoamyl alcohol extraction is repeated once again. Clean RNA is precipitated out of the solution.

Alcohol Precipitation

Two volumes (1000 l) ice cold absolute ethanol is added to the mixture. The tube is centrifuged for 15 minutes at 15,000×g in a microcentrifuge. The supernatant is decanted and discarded and the precipitated RNA is redissolved in 100 l DEPC treated water then re-exposed to the RNA+8-MOP.

Isolation of the Psoralentated RNA Fragments Using HPLC

All components, glassware and reagents are prepared so that they are RNAase free. The HPLC is set up with a Dionex DNA PA-100 package column. The psoralenated RNA:DNA hybrid is warmed to 4° C. The psoralenated RNA is applied to HPLC followed by olignucleotide analysis, as described in the following section entitled "Olignucleotide Analysis by HPLC." The collected fractions will represent:

a) 5'CUAGA CUGGAGG3', where is pseudouridine (SEQ ID NO:1)
b) Furan sided 5'CUPsoralenAGA CUGGAGG3' monoadducts(SEQ ID NO:2)
c) 5'XXXXXCCUCCAGAUCUAGXXXXX3'(SEQ ID NO:3)
d) 5'XXXXXCCUCCAGAUCUPsoralenAGXXXXX3' (SEQ ID NO: 4)

The fractions are stored at 4° C. in new, RNAase free snapped microcentrifuge tubes and stored at –20° C. if more than four weeks of storage is required.

Identification of the RNA Fragments Represented by Each Peak Fraction Collected by HPLC Using Polyacrylamide Gel Electrophoresis (PAGE)

The electrophoresis unit is set up in a 4° C. refrigerator. A gel is selected with a 2 mm spacer. Each 5 μl of HPLC fraction is diluted to 10 μl with Loading Buffer. 10 μl of each diluted fraction is loaded into appropriately labeled sample wells. The tracking dye is loaded in a separate lane and electrophoresis is run as described in the following section entitled "Polyacrylamide Gel Electrophoresis (PAGE) of Psoralenated RNA Fragments." After the electrophoresis run is complete, the electrophoresis is stopped when the tracking dye has reached the edge of the gel. The apparatus is disassembled. The gel-glass panel unit is placed on the UV light box. UV lights are turned on. The RNA bands are identified. The bands will appear as denser shadows under UV lighting conditions.

Extraction of the RNA From the Gel

Each band is excised with a new sterile and RNAase free scalpel blade and transferred into a new 1.5 ml snap capped microcentrifuge tube. Each gel is crushed against the walls of the microcentrifuge tubes with the side of the scalpel blade. A new blade is used for each sample. 1.0 ml of 0.3M sodium acetate is added to each tube and eluted for at least 24 hours at 4° C. The eluate is transferred to a new 0.5 ml snap capped polypropylene microcentrifuge tube with a micropipet. A new RNAase free pipette tip is used for each tube and the RNA with ethanol is precipitated out.

Ethanol Precipitation

Two volumes of ice cold ethanol is added to each eluate then centrifuged at 15,000×g for 15 minutes in a microcentrifuge. The supernatants are discharged and the precipitated RNA is re-dissolved in 100 l of DEPC treated DI water. The RNA is stored in the microcentrifuge tubes at 4° C. until needed. The tubes are stored at –20° C. if storage is for more than two weeks. The following is the assumed order of rate of migration for each fragment in order from fastest to slowest:

a) 5'CUAGA CUGGAGG3'
b) Furan sided 5'CUPsoralenAGA CUGGAGG3' monoadducts.
c) 5'XXXXXCCUCCAGAUCUAGXXXXX3'
d) 5'XXXXXCCUCCAGAUCUPsoralenAGXXXXX3'

The tubes are labeled containing the remainder of each fraction with the presumed chemical sequence and stored at –20° C.

Ethanol Precipitation of RNA

RNA oligonucleotide fragments are precipitated, and all glassware is cleaned to remove any traces of RNase as described in the following section entitled "Inactivation of RNases on Equipment, Supplies, and in Solutions." All solutions are stored in RNAase free glassware and introduction of nucleases is prevented. Absolute ethanol is stored at 0° C. until used. Micropipetors are used to add two volumes of ice cold ethanol to nucleic acids that are to be precipitated in microcentrifuge tubes. Capped microcentrfuge tubes are placed into the microfuge and spun at 15,000×g for 15 minutes. The supernatant is discarded and precipitated RNA is re-dissolved in DEPC treated DI-water. RNA is stored at 4° C. in microcentrifuge tubes until ready to use.

Ligation of RNA Fragments 2 and 3

All glassware is cleaned to remove any traces of RNase as described in the following section entitled "Inactivation of RNases on Equipment, Supplies, and in Solutions." The following is added to a new 1.5 ml polypropylene snap capped microcentrifuge tube using a 100–1000 μl pipet and a new sterile pipet tip is used for each solution:

| | |
|---|---|
| Fragment 2 (3.0 nM) | 125.0 μl |
| Fragment 3 (3.0 nM) | 125.0 μl |
| Reaction buffer | 250.0 μl |
| RNA T4 ligase (9–12 U/ml) | 42 μl |
| Reaction Buffer | |
| RNase free DI-water | 90.00 ml |
| Tris-HCl (50 mM) | 0.79 g |
| MgCl2 (10 mM) | 0.20 g |
| DTT (5 mM) | 0.078 g |
| ATP (1 mM) | 0.55 g |
| pH to 7.8 with HCL | |
| RNase free DI-water | QS to 100.00 ml |

The mixture is gently mixed and the RNA is melted by incubating the mixture at 16° C. for one hour in a temperature controlled refrigerated chamber. RNA is precipitated out of the solution immediately after the incubation is completed.

Alcohol Precipitation

Two volumes (~1000 μl) of ice cold absolute ethanol are added to the reaction mixture. The microcentrifuge tube is placed in a microcentrifuge at 15,000×g for 15 minutes. The supernate is decanted and discarded and the precipitated RNA is re-dissolve in 100 μl DEPC treated water. The mixture is electrophoresed as described in the following section entitled "Polyacrylamide Gel Electrophoresis (PAGE) of Psoralenated RNA Fragments." The following is the assumed order of rate of migration for each fragment in order from fastest to slowest:

a) Frag. 2
  5'CUAGA CUGGAGG3'—OH

Psoralen b) Frag. 3
  5'UCCUGUGT CGAUCCACAGAAUUCGCACC-Puromycin (SEQ ID NO: 5)

c) Frag 2+3
  5'CUAGA ψCUGGAGGUCCUGUGTψCGAUCCA CAGAAUUCGCACCPuromycin (SEQ ID NO: 6)

Psoralen

Each fraction is isolated by UV shadowing, the bands are cut out, the RNAs are eluted from the gels and the RNA elute is precipitated out as described in the following section entitled "Polyacrylamide Gel Electrophoresis (PAGE) of Psoralenated RNA Fragments." The ligation procedure is repeated with any residual unligated fragment 2 and 3 fractions. The ligated fractions 2 and 3 are pooled and stored in a small volume of RNase free DI-water at 4° C.

Ligation of RNA Fragment 1 with Fragment 2+3

All glassware is cleaned to remove any traces of RNase as described in the following section entitled "Inactivation of RNases on Equipment, Supplies, and in Solutions." The following is added to a new 1.5 ml polypropylene snap capped microcentrifuge tube. A 100–1000 μl pipet and new tip is used for each solution:

| | |
|---|---|
| Fragment 2 + 3 (3.0 nM) | 125.0 μl |
| Reaction buffer | 250.0 μl |
| T4 Polynucleotide Kinase (5–10 U/ml) | 1.7 μl |

-continued

| | |
|---|---|
| Reaction Buffer | |
| RNase free DI-water | 90.00 ml |
| Tris-HCl (40 mM) | 0.63 g |
| MgCl2 (10 mM) | 0.20 g |
| DTT (5 mM) | 0.08 g |
| ATP (1 mM) | 0.006 g |
| pH to 7.8 with HCL | |
| RNase free DI-water | QS to 100.00 ml |

The RNA is gently mixed then melted by heating the mixture to 70° C. for 5 minutes in a heating block. The mixture is cooled to room temperature over a two hour period and the RNAs is allowed to anneal in a tRNA configuration. The RNA is precipitated out of the solution.

Alcohol Precipitation

Two volumes (~1000 μl) if ice cold absolute ethanol are added to the reaction mixture. The microcentrifuge tube is placed in a microcentrifuge at 15,000×g for 15 minutes. The supernate is decanted and discarded and the precipitated RNA is re-dissolved in 100 μl DEPC treated water. The mixture is electrophoresed as described in the following section entitled "Polyacrylamide Gel Electrophoresis (PAGE) of Psoralenated RNA Fragments." The following is the assumed order of rate of migration for each fragment in order from fastest to slowest:

a) Frag. 1
  5'GCGGAUUUAGCUCAGDDGGGAGAGCGC-CAGACU3' b) Frag 2+3
  5'CUAGA ψCUGGAGGUCCUGUGTψCGAUCCA CAGAAUUCGCACC Puromycin

Psoralen c) Frag. 1+2+3

Psoralen

Each fraction is isolated by UV shadowing, the bands are cut out, the RNAs are eluted from the gels and the RNA elute is precipitated out as described in the following section entitled "Polyacrylamide Gel Electrophoresis (PAGE) of Psoralenated RNA Fragments." The ligation procedure is repeated with the unligated Fragment 1 and the 2+3 Fraction. The ligated fractions 2+3 are pooled and stored in a small volume of RNase free DI-water at 4° C.

Final RNA Ligation

The following is added to a new 1.5 ml polypropylene snap capped microcentrifuge tube. A 100–1000 μl pipet and new tip is used for each solution:

| | |
|---|---|
| Fragment 1 + 2 + 3 (3.0 nM) | 250 μl |
| reaction buffer | 250 μl |
| RNA T4 ligase (44 μg/ml) | 22 μg |

The mixture is incubated at 17° C. in a temperature controlled refrigerator for 4.7 hours. Immediately after the incubation the tRNA is precipitated out as described in step 6.2 above and the tRNA is isolated by electrophoresis as described in the following section entitled "Polyacrylamide Gel Electrophoresis (PAGE) of Psoralenated RNA Fragments." The tRNA is pooled in a small volume of RNase free water and stored at 4° C. for up to two weeks or stored at −20° C. for periods longer than two weeks.

Polyacrylamide Gel Electrophoresis (PAGE) of Psoralenated RNA Fragments

Acrylamide Gel Preparation

All reagents and glassware must be RNAase free as described in the following section entitled "Inactivation of RNases on Equipment, Supplies, and in Solutions." The gel apparatus is assembled to produce a 4 mm thick by 20 cm×42 cm square gel. 29 parts acrylamide with 1 part ammonium crosslinker are mixed at room temperature with the appropriate amount of acrylamide solution in an RNAase free, thick walled Erlenmeyer flask.

| Acrylamide Solution | |
|---|---|
| urea (7M) | 420.42 g |
| TBE (1X) | QS to 1L |
| 5X TBE | |
| 0.455M Tris-HCl | 53.9 g |
| 10 mM EDTA | 20 ml of 0.5M |
| RNAase free DI water | 900 ml |
| pH with boric acid to | pH 9 |
| QS with RNAase free DI water to | 1L |

The mixture is degassed with vacuum pressure for one minute. The appropriate amount of TEMED is added, mixed gently, and then the gel mixture is poured between the glass plates to within 0.5 cm of the top. The comb is immediately inserted between the glass sheets and into the gel mixture. An RNAase free gel comb is used. The comb should produce wells for a 5 mm wide dye lane and 135 mm sample lanes. The gel is allowed to polymerize for about 30–40 minutes then the comb is carefully removed. The sample wells are rinsed out with a running buffer using a micropipet with a new pipet tip. The wells are then filled with running buffer.

Sample Preparation

An aliquot of the sample is suspended in loading buffer in a snap capped microcentrifuge tube and vortex mixed. Indicator dye is not added to the sample.

Loading Buffer

| Urea (7M) | 420.42 g |
|---|---|
| Tris HCl (50 mM) | 7.85 g |
| QS with RNAase free D-H2O | to 1L |

Electrophoresis Run

The maximum volume of RNA/loading buffer solution is loaded into the 135 mm sample wells and the appropriate volume of tracking dye in 5 mm tracking lane. The samples are electrophoresed in a 5° C. refrigerator. The electrophoresis is stopped when the tracking dye has reached the edge of the gel. Disassemble the apparatus. Glass panels are not removed the from the gel. The gel-glass panel unit is placed on a UV light box. With UV filtering goggles in place, the UV lights are turned on. The RNA bands are identified. They appear as denser shadows under UV lighting conditions. The RNA is extracted from the gel. Each bands is excised with a new sterile and RNAase free scalpel blade and each band is transferred into a new 1.5 ml snap capped microcentrifuge tube. Each gel is crushed against the walls of the microcentrifuge tubes with the side of the scalpel blade. A new blade is used for each sample. 1.0 ml of 0.3M sodium acetate is added to each tube and eluted for at least 24 hours at 4° C. The eluate is transferred to a new 0.5 ml snap capped polypropylene microcentrifuge tubes with a micropipet with a new RNAase free pipet tip for each tube. Two volumes of ice cold ethanol is added to each eluate, then centrifuged at 15,000×g for 15 minutes in a microcentrifuge. The supernatants are discarded and the precipitated RNA is redissolved in 100 µl of DEPC treated DI water. The RNA is stored in the microcentrifuge tubes at 4° C. until needed.

Olignucleotide Analysis by HPLC

HPLC purification of the RNA oligonucleotides is best effected using anion exchange chromatography. Either the 2'-protected or 2'-deprotected forms can be chromatographed. The 2'-protected form offers the advantage of minimizing secondary structure effects and provides resistance to nucleases. If the RNA is fully deprotected, sterile conditions are required during purification.

Deprotection of 2'Orthoester Protected RNA

The tubes are centrifuged at 15,000×g for 30 seconds or until the RNA pellet is at the bottom. 400 µl of pH 3.8 deprotection buffer is added to each tube of RNA.

Deprotection Buffer

Acetic acid (100 mM) is adjusted to pH 3.8 with tetramethylethylenediamine (TEMED). The pellet is completely dissolved in the buffer by drawing in and out of a pipette. The tubes are vortexed for 10 seconds and centrifuged at 15,000×g. The tubes are incubated in a 60° C. water bath for 30 minutes. The samples are lyophilized before use.

HPLC Column Conditions

A 4×250 mm column (DNAPAC PA, No. 043010) packed with Dionex (800)-DIONEX-0 (346–6390), with a capacity of 40 optical density units (ODU) at 260 nm is installed. The column temperature is set to 54° C. The injection volume is adjusted such that 5 µl produces approximately 0.20 ODU.

Elution Buffers

| Condition | Buffer A | Buffer B |
|---|---|---|
| Sodium perchlorate | (5 mM) | (300 mM) |
| | 2.8 g | 168.0 g |
| Tris-HCl | 2.4 g | 2.4 g |
| Acetonitrile (2%) | 80.0 ml | 80.0 ml |
| DI Water | 3900 ml | 900 ml |
| Adjusted pH | 8.0 with HCL | 8.0 with HCL |
| q.s. | 4000 ml | 4000 ml |

HPLC Gradient

A 30% to 60% gradient of Buffer B for oligos 17–32 base pairs long is provided:

| Time (minutes) | Flow (ml/min) | % A | % B | Curve |
|---|---|---|---|---|
| 0 | 1.5 | 100 | 0 | * |
| 1 | 1.5 | 100 | 0 | 6 |
| 3 | 1.5 | 70* | 30* | 6 |
| 15 | 1.5 | 40* | 60* | 6 |
| 15.5 | 2.5 | 0 | 100 | 6 |
| 17 | 2.5 | 0 | 100 | 6 |
| 17.25 | 2.5 | 100 | 0 | 6 |
| 23 | 2.5 | 100 | 0 | 6 |
| 23.1 | 1.5 | 100 | 0 | 6 |
| 24 | 1.5 | 100 | 0 | 6 |
| 25 | 0.1 | 100 | 0 | 6 |

*% values that can be changed to modify the gradient. Typical gradients are 0–30%, 20–50%, 30–60%, and 40–70% of Buffer B.

Gradient Selection

The gradient is selected based upon the number of bases, as follows:

| Number of bases | Gradient |
|---|---|
| 0–5 | 0–30 |
| 6–10 | 10–40 |
| 11–16 | 20–50 |
| 17–32 | 30–60 |
| 33–50 | 40–70 |
| >50 | 50–80 |

After HPLC, the target samples are collected and the RNA concentration is determined with a spectrophotometer at 260 nm. The samples are stored at −70° C.

Inactivation of RNases on Equipment, Supplies, and in Solutions

Glassware is treated by baking at 180° C. for at least 8 hours. Plasticware is treated by rinsing with chloroform. Alternatively, all items are soaked in 0.1% DEPC.

Treatment with 0.1% DEPC 0.1% DEPC is prepared. DI water is filtered through a 0.2 μM membrane filter. The water is autoclaved at 15 psi for 15 minutes on a liquid cycle. 1.0 g (wt/v) DEP C/liter of sterile filtered water is added.

Glass and Plasticware

All glass and plasticware is submerged in 0.1% DEPC for two hours at 37° C. The glassware is rinsed at least 5× with sterile DI water. The glassware is heated to 100° C. for 15 minutes or autoclaved for 15 minutes at 15 psi on a liquid cycle.

Electrophoresis Tanks Used for Electrophoresis of RNA

Tanks are washed with detergent, rinsed with water then ethanol and air dried. The tank is filled with 3% (v/v) hydrogen peroxide (30 ml/L) and left standing for 10 minutes at room temperature. The tank is rinsed at least 5 times with DEPC treated water.

Solutions

All solutions are made using Rnase free glassware, plastic ware, autoclaved water, chemicals reserved for work with RNA and RNase free spatulas. Disposable gloves are used. When possible, the solutions are treated with 0.1% DEPC for at least 12 hours at 37° C. and then heated to 100° C. for 15 minutes or autoclaved for 15 minutes at 15 psi on a liquid cycle.

RNA Translation

2 μl of gastroinhibitory peptide (GIP) mRNA at a concentration of 20 μl/ml is placed in a 250 μl snapcap polypropylene microcentrifuge tube. 35 μl of rabbit reticulocyte lysate (available commercially from Promega) is added. 1 μl of amino acid mixture which does not contain methionine (available commercially from Promega) is added. 1 μl of 35S methione or unlabeled methionine is added. Optionally, 2 ml of luciferase may be added to some tubes to serve as a control.

SATA is added to the experimental tubes. Control tubes which do not contain SATA are also prepared. The quantity of SATA used is approximately between 0.1 μg to 500 μg, preferably between 0.5 μg to 50 μg. 1 μl of Rnasin at 40 units/ml is added. Nuclease free water is added to make a total volume of 50 μl.

For proteins greater than approximately 150 amino acids, the amount of tRNA may need to be supplemented. For example, approximately 10–200 μg of tRNA may be added. In general, the quantity of the SATA should be high enough to effectively suppress stop or pseudo stop codons. The quantity of the native tRNA must be high enough to out compete the SATA which does not undergo dynamic proofreading under the action of elongation factors.

Each tube is immediately capped, parafilmed and incubated for the translation reactions at 30° C. for 90 minutes. The contents of each reaction tube is transferred into a 50 μl quartz capillary tube by capillary action. The SATA is crosslinked with mRNA by illuminating the contents of each tube with 2–10 J/cm2~350 nm wavelength light, as per Gasparro et al. (Photochem. Photobiol. 57:1007 (1993), herein incorporated by reference). Following photo-crosslinking, the contents of each tube is transferred into a new snapcap microfuge tube. The ribosomes are dissociated by chelating the calcium cations by adding 2 μl of 10 mM EDTA to each tube. Between each step, each tube is gently mixed by stirring each component with a pipette tip upon addition.

The optimal RNA for a translation is determined prior to performing definitive experiments. Serial dilutions may be required to find the optimal concentration of mRNA between 5–20 μg/ml.

| Reagent | 1 | 2 | 3 | 4 |
|---|---|---|---|---|
| Rabbit reticulocyte lysate (35 μl) | + | + | + | + |
| Amino acid mixture minus methionine (1 μl of 1 mM) | + | + | + | + |
| $^{35}$S Methionine (1 μl of 1,200 Ci/mmol) | + | − | − | + |
| Methionine (unlabeled) | − | + | + | − |
| GIP mRNA (2 μl of 20 μg/ml) | + | − | − | − |
| $^{32}$P GIP mRNA (2 μl of 20 μg/ml) | − | + | + | − |
| Rnasin (1 μl of 40 U/μl) | + | + | + | + |
| SATA | − | − | − |  |
| Water, nuclease free (q.s. to 50 μl) | + | + | + | + |

SDS-Page electrophoresis is performed on each sample, as described above. Autoradiography on the gel is performed, as described by Sambrook et. al., Molecular Cloning, A Laboratory Manual, $2^{nd}$ ed., Coldspring Harbor Press (1989), herein incorporated by reference.

While a number of preferred embodiments of the current invention and variations thereof have been described in detail, other modifications and methods of use will be readily apparent to those of skill in the art. Accordingly, it should be understood that various applications, modifications and substitutions may be made without departing from the spirit of the invention or the scope of the claims.

What is claimed is:

1. A method for identifying a desired protein or nucleic acid molecule comprising:
   providing at least two candidate mRNA molecules, each of said mRNA molecules comprising a crosslinker;
   translating at least two of said candidate mRNA molecules to generate at least one translated protein;
   linking at least one of said candidate mRNA molecules to its corresponding translated protein via said crosslinker, to form at least one cognate pair;
   identifying one or more of said cognate pairs based upon the properties of said translated protein or said mRNA molecule.

2. The method of claim 1, wherein said translating is performed in vitro.

3. The method of claim 1, wherein said translating is performed in situ.

4. The method of claim 1, wherein said cognate pair is selected based upon ligand binding.

5. The method of claim 4, wherein said ligand binding is based on positive selection.

6. The method of claim 4, wherein said ligand binding is based on negative selection.

7. The method of claim 1, further comprising the step of selecting said desired nucleic acid molecule, wherein the step of selecting said desired nucleic acid comprises:
   providing an array of nucleic acids, wherein said nucleic acids are placed in a predetermined position;
   hybridizing at least one of said cognate pairs onto said array;
   reacting said at least one of said cognate pairs with one or more binding agents; and
   selecting said desired nucleic acid molecule based upon the reaction to said one or more binding agents.

8. The method of claim 7, wherein said reaction is selected from the group consisting of one or more of the following: ligand binding, immunoprecipitation, and enzymatic reactions.

9. The method of claim 8, wherein said ligand binding uses a ligand that is selected from the group consisting of one or more of the following: proteins, nucleic acids, chemical compounds, polymers and metals.

10. The method of claim 1, wherein said crosslinker is placed on a codon.

11. The method of claim 1, wherein said crosslinker is placed on a stop codon.

12. The method of claim 1, further comprising the step of selecting said desired nucleic acid molecule, wherein the step of selecting said desired nucleic acid comprises:
    providing an array of nucleic acids,
    hybridizing said at least one of said cognate pairs onto said array;
    exposing said at least one of said cognate pairs to one or more binding agents; and
    selecting said desired nucleic acid molecule based upon the presence or absence of a reaction to said one or more binding agents.

13. The method of claim 1, further comprising determining a DNA sequence corresponding to the amino acid sequence of said translated protein, comprising:
    providing an array of two or more DNA sequences, wherein said two or more DNA sequences are placed in a predetermined position;
    exposing said array to said one or more cognate pairs, wherein said one or more cognate pairs comprises an mRNA portion and a protein portion;
    hybridizing the mRNA portion of said one or more cognate pairs onto said array;
    exposing the protein portion of said one or more cognate pairs to a binding agent, thereby producing a reaction or a non-reaction; and
    selecting said desired protein based upon the reaction or non-reaction to said binding agent, thereby determining a DNA sequence corresponding to the amino acid sequence of said translated protein.

14. The method of claim 1, wherein at least one of said candidate mRNA molecules and at least one said translated protein is linked by a tRNA molecule selected from the group consisting of an unmodified tRNA, a modified tRNA and a tRNA analog.

15. The method of claim 14, wherein said tRNA molecule is connected to said translated protein by ribosomal peptidyl transferase.

16. The method of claim 14, wherein said tRNA is connected to the mRNA through an ultraviolet-induced crosslink.

17. The method of claim 16, wherein the tRNA molecule is connected to the mRNA between an anticodon of said tRNA molecule and a codon of the RNA message.

18. The method of claim 14, wherein said tRNA molecule is connected to the mRNA by a psoralen cross link.

19. The method of claim 18, further comprising producing said psoralen cross link by irradiating a furan-sided psoralen monoadduct using a wavelength in the range of about 320 nm to about 400 nm.

20. The method of claim 14, wherein said tRNA molecule is connected to the mRNA by using a psoralen monoadduct.

21. The method of claim 20, wherein said psoralen monoadduct is generated by forming crosslinks and photo reversing said crosslinks or by using visible light.

22. The method of claim 14, wherein said tRNA molecule has a stable peptide acceptor.

23. The method of claim 14, wherein said tRNA molecule is operable to accept a peptide chain and hold said chain in a stable manner, such that peptidyl transferase cannot detach it.

24. The method of claim 14, wherein said tRNA molecule comprises a moiety which binds to the ribosome, accepts the peptide chain, and then does not act as a donor in the next transpeptidation.

25. The method of claim 24, wherein said moiety is selected from the group consisting of one or more of the following: a 2' ester on a 3' deoxy adenosine, an amino acyl $tRNA_{ox-red}$ and a puromycin.

26. The method of claim 14, further comprising attaching an amino acid or amino acid analog to the 3' end of said tRNA molecule by a stable bond to generate a stable aminoacyl tRNA analog.

27. The method of claim 14, wherein said tRNA molecule is connected to the mRNA by thiouracil.

28. The method of claim 1, wherein, after the linking step, the translated protein is released from a ribosome in which it is translated.

29. The method of claim 28, wherein the translated protein is released from the ribosome by denaturing the ribosome.

30. A method for identifying a desired translated protein comprising:
    providing at least two candidate mRNA molecules, each of said mRNA molecules comprising a crosslinker;
    translating at least two of said candidate mRNA molecules to generate at least one translated protein;

coupling at least one of said candidate mRNA molecules to its corresponding translated protein to form at least one cognate pair, and identifying the desired translated protein by identifying one or more of said cognate pairs based upon the properties of said translated protein or said mRNA molecule.

31. A method for identifying a desired nucleic acid comprising:

providing at least two candidate mRNA molecules, each of said mRNA molecules comprising a crosslinker;

translating at least two of said candidate mRNA molecules to generate at least one translated protein;

coupling at least one of said candidate mRNA molecules to its corresponding translated protein to form at least one cognate pair, and identifying the desired nucleic acid by identifying one or more of said cognate pairs based upon the properties of said translated protein or said mRNA molecule.

* * * * *